Figure 1:
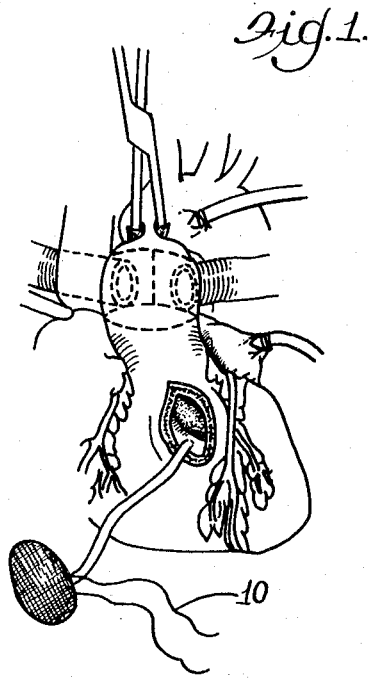

United States Patent [19]

Bokros et al.

[11] 4,204,542
[45] * May 27, 1980

[54] MULTISTRAND CARBON COATED SUTURES

[75] Inventors: Jack C. Bokros, Alpine; Hong S. Shim; Axel D. Haubold, both of San Diego, all of Calif.

[73] Assignee: CarboMedics, Inc., San Diego, Calif.

[*] Notice: The portion of the term of this patent subsequent to Aug. 14, 1996, has been disclaimed.

[21] Appl. No.: 853,848

[22] Filed: Nov. 22, 1977

Related U.S. Application Data

[63] Continuation-in-part of Ser. No. 821,602, Aug. 3, 1977, Pat. No. 4,164,045.

[51] Int. Cl.² .............................................. A61L 17/00
[52] U.S. Cl. .................. 128/335.5; 428/368; 3/1

[58] Field of Search ...................... 128/335.5; 428/368, 428/367, 375; 3/1

[56] References Cited

U.S. PATENT DOCUMENTS

| | | | |
|---|---|---|---|
| 3,685,059 | 8/1972 | Bokros et al. | 128/1 R X |
| 3,754,069 | 8/1973 | Adams et al. | 128/335.5 X |
| 3,952,334 | 4/1976 | Bokros et al. | 3/1.5 X |

*Primary Examiner*—Clifford D. Crowder
*Attorney, Agent, or Firm*—Fitch, Even & Tabin

[57] ABSTRACT

Multistrand carbon coated sutures comprising a plurality of small diameter fibers having a tensile modulus of at least about $2 \times 10^6$ psi, and a thin, smooth, adherent, isotropic carbon coating on the substrate fiber having particular properties including a tensile fracture strain of at least about 5%.

5 Claims, 3 Drawing Figures

MULTISTRAND CARBON COATED SUTURES

This application is a continuation in part of copending application Ser. No. 821,602, filed Aug. 3, 1977, now U.S. Pat. No. 4,164,045.

The present invention relates to multistrand sutures adapted for prolonged or permanent implantation in a living body, and, more particularly is directed to multistrand sutures having a carbon coating which may be utilized in surgical procedures.

The employment of pyrolytic carbon coatings to produce biocompatable and thromboresistant surfaces has produced substantial advancement in the medical field and is described, for example, in U.S. Pat. Nos. 3,526,005 issued Sept. 1, 1970 and U.S. Pat. No. 3,685,059 issued Aug. 22, 1972. These patents generally describe deposition of pyrolytic carbon coatings, usually from a diluted hydrocarbon atmosphere at atmospheric pressure. Various other techniques have been developed for depositing vapor coatings, for example, as by vacuum vapor deposition (VVD) which is also sometimes referred to as vacuum metalizing, physical vapor deposition or evaporative coating, sputtering or as by ion-plating techniques [e.g., see Marinkovic, et al., Carbon, 14, 329 (1976); cited references are incorporated herein by reference]. Coatings deposited by such techniques, which are generally referred to herein as vapor-deposited carbon coatings, have been utilized in prosthetic devices, as described in U.S. Pat. No. 3,952,334, and may be applied to fiber structures in provision of prosthetic elements such as artificial tendons and patch grafts. However, there is still a need to provide additional fiber prosthetic elements such as sutures with biocompatability.

Conventionally, sutures used in many surgical procedures are made of material which is capable of being absorbed by the body over a period of time. However, a number of surgical procedures utilize, or could benefit from, sutures which are intended to be permanently retained in the body to provide a supportive or structural function. For example, sutures may be used to connect a prosthetic heart valve to heart tissue, or to connect synthetic or biologic grafts into the vascular system.

Figure 2:
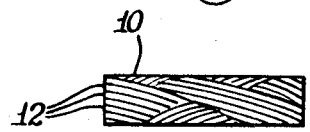
Figure 3:
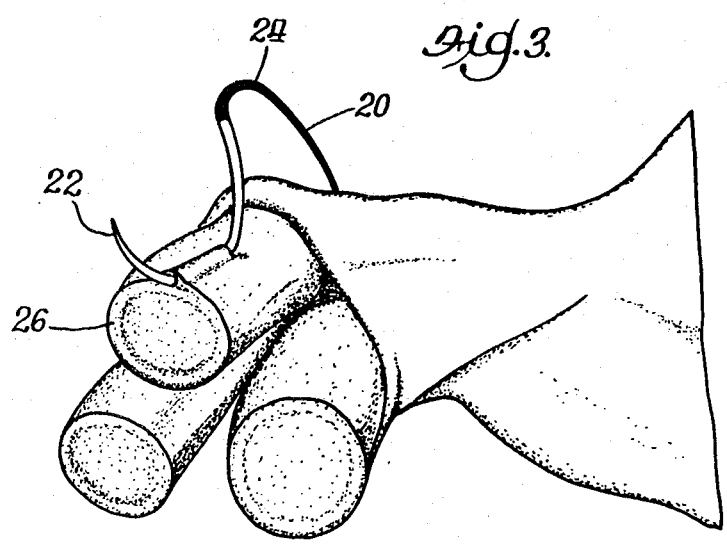

Accordingly, it is an object of the present invention to provide sutures which are suitable for prolonged or permanent implantation in a living body and which are capable of providing substantial structural strength. It is a further object to provide improved sutures for reconstructive surgery. These and other objects of the invention will be readily apparent from the following detailed description and the accompanying drawings of which:

FIG. 1 is a view of one embodiment of a multistrand suture in open heart operative procedure in accordance with the present invention, FIG. 2 is an enlarged view of a portion of the sutures illustrated in FIG. 1, and FIG. 3 is a view of another embodiment of suture in operative procedure in accordance with the present invention.

Generally, the present invention is directed to flexible, biologically compatible multistrand sutures suitable for prolonged or permanent implantation in a living body. The multistrand sutures may desirably be provided in braided or helically wound, stranded form, and may be provided with a range of suture diameters for different surgical applications.

The flexible multistrand sutures comprise a plurality of intertwined carbon-coated, organopolymeric fibers of particular characteristics. Generally, the sutures will comprise at least about 7 such fibers. The organopolymeric fibers are of relatively small diameter which are able to sustain the functional stresses intended for the particular suture utilization and provide for a desired high degree of tensile strength and flexibility without straining more than about 5 percent. The individual fibers of the multifiber suture should generally best have a major diameter dimension of less than about 25 microns, and a minor diameter dimension of at least about 5 microns, although fibers as small as 1 micron might be used in certain applications. By "major diameter dimension" is meant the widest dimension of the fiber in a direction orthogonal to the longitudinal axis of the fiber, and by "minor diameter dimension" is meant the narrowest dimension of the fiber in a direction orthogonal to the longitudinal axis of the fiber. Of course, for a fiber of circular cross section, the major and minor diameter dimensions will be the same, but it should be appreciated that the invention does contemplate fibers of non-circular cross-section. However, deviation from circular fiber cross-sections generally tends to lead to stiffer sutures because of the increased interfibral friction and increased forces required for bending and unbending of the fiber filaments.

In the sutures of the present invention, a plurality of individual, small carbon-coated fibers are combined to provide a flexible strand having a predetermined high degree of flexibility and strength as well as beneficial biologically compatible properties of a carbon coating.

The relatively high degree of flexibility of the composite multistrand sutures is due primarily to the bending of the individual fibers with maintenance of the integrity of a carbon coating on the fibers. The radius of curvature of the individual fibers that will provide a degree of bending without fracture of an adherent carbon coating having a relatively high tensile fracture strain of at least 5 percent, is determined by the diameter of the fiber. The minimum radius of curvature R for a given fiber is approximately represented as follows:

$$R = \frac{\text{Diameter of the fiber}}{2 \times \text{allowable strain}}$$

For example, for a fiber diameter of about 10 microns ($=10^{-3}$ cm), the allowable radius of curvature R at an allowable strain of 5% is:

$$R = \frac{1 \times 10^{-3} \text{ cm}}{2 \times (5 \times 10^{-2})} = .01 \text{ cm}$$

Accordingly, the relatively small fiber diameters of the fibers utilized, provides the composite sutures with substantial flexibility range without cracking the specified carbon coating (which is provided in an isotropic form capable of withstanding at least about 5% strain without fracture). Smaller fibers are preferred for increased flexibility, and the lower limit of diameter is determined by handling and coating parameters.

Certain physical parameters characterize the organopolymeric substrate fibers of the present sutures. In this connection, the fibers should be of an organopolymeric material having a tensile strength of at least about 20,000 psi and should be fabricated of medical grade materials. Generally, the fibers will best have a high degree of axial orientation. The modulus is an important parameter, and the organopolymeric fibers should have a tensile modulus of elasticity of about $2\times10^6$ psi or more. Polyethylene terephthalate fibers, such as those sold under the trade name Dacron, are particularly preferred because of the biocompatability of such polyester fibers ["Implants in Surgery", D. Williams, et al., W. B. Saunders Company, Ltd., London (1973)], their strength (e.g., 50,000 to 99,000 psi breaking strength) and stiffness (e.g., modulus of elasticity of about $2\times10^6$ psi), which may be almost equal to that of the isotropic carbon coating. Such a high modulus, high strength material can support a relatively large load without straining more than 5% (such that the carbon coating would break). Polyethylene terephthalate fibers may be, for example, about three times tougher and five times stiffer than poly(tetrafluoroethylene).

As indicated, the present sutures comprise a plurality of (generally coaxial) individual, small diameter carbon-coated fibers. Usually such multistrand sutures will comprise at least 7 and preferably at least 15 individual fibers, with the individual fibers desirably being formed into a braided or helically wound or corded form.

In suturing applications where it is desirable to have permanent tissue affixation to the suture and correspondingly limited suture mobility, sutures comprising a braided fiber array may be utilized. However, where tissue ingrowth suture immobility is not particularly appropriate, sutures comprising a twisted strand of a plurality of individual carbon coated fibers may be more desirable.

In addition to poly(ethylene terephthalate), other suitable high strength, high modulus organpolymeric substrate materials, provided their biocompatability is demonstrated, include various so-called "high temperature polymers" which have generally been developed in the last decade, such as the high modulus and high tensile strength aromatic polyimides and aromatic polyamides. High temperature polymer fibers which may be used herein exhibit thermal stability at temperatures of 300° C. and higher and are generally characterized as high temperature, high molecular weight, aromatic, nitrogen-linked polymers. Such polymers are well known in the polymer art, and examples of such high temperature polymers include ordered aromatic copolyamides, such as the reaction product of phenylenebis (amino-benzamide) and isophthaloyl chloride, all-aromatic polybenzimidazoles, such as poly [2,2' (m-phenylene)-5,5' (6,6' benzimidazoles)], polyozadiazoles, poly (n-phenyl triazoles), polybenzobenzimidazoles, polyimides and poly (amide-imide) resins. Of course, the biocompatability of such materials should be tested, and medical implant grade materials should be used for prosthetic implants. The preferred organopolymeric fibers contemplated for use herein are medical grade polyethylene terephthalates, but various conventional high temperature polymer fibers commercially available, such as fibers sold under the name Kevlar by DuPont, and having a modulus of about $10\times10^6$ psi may prove useful.

As previously indicated, the individual fibers of the sutures of the present invention are provided with an adherent isotropic carbon coating of particular properties including high fracture strain and specified isotropy and thickness.

The carbon coatings may be provided on suitable substrate fibers by vapor-deposition techniques such as described in the previously referenced U.S. Pat. No. 3,952,334, to produce strongly adherent carbon coatings which have outstanding tissue and blood compatability. The carbon should be provided in a very highly elastic form having 5 percent or more fracture strain.

The individual fibers will typically be about 10 microns in diameter. The smaller the fiber, the smaller the radius of curvature it can sustain without cracking the specified carbon coating, which is required to be capable of sustaining at least about 5% elastic strain before fracture, as previously discussed. In view of the small diameter of the fibers used, it is a desirable advantage that the carbon coating may be provided either by coating the fibers before assembly in multistrand suture form, or by coating the suture fiber assembly. However, it will be appreciated that braiding or twisting of previously coated fibers may generally tend to introduce bending strain, while coating of previously braided or twisted multistrand suture substrate fibers produces a minimum of strain in the finished composite structure and therefore is particularly preferred, particularly in braided suture structures.

In any event, the entire suture structure is provided with a carbon layer of particular properties and may be applied while using coating technology, such as described in U.S. Pat. No. 3,952,334. Further, in this connection, the carbon coating should be at least about 1000 Å (0.1 micron) thick, should be adherent, and in order to provide for large fracture strains, should have BAF (Bacon Anisotropy Factor) of about 1.3 or less and preferably about 1.2 or less. Generally, a coating thickness of about 1000 to 7000 Å and preferably from about 3000 to about 5000 Å of intermediate density of carbon (at least about 1.6 gm/cm$^3$) is employed; greater thicknesses tend to crack and flake. Preferably, the vapor-deposited carbon has a density of about 1.8 gm/cm$^3$, and the density should not exceed about 2.0 gm/cm$^3$. Such vapor-deposited carbon exhibits biocompatible properties and also may be provided with excellent adherence to the small polymer fibers of the high modulus organopolymeric fiber substrate. As a result, the carbon coated fibers exhibit excellent properties for use in sutures and are considered to be fully acceptable for implantation within the human body in flexible and tensile service.

Through the design provision of a limited tensile strain in the individual organopolymeric substrate fibers of not more than 5% under intended conditions of use, the integrity of the carbon coating is generally preserved for prolonged or permanent implantation service. In this regard, as previously indicated, small oriented polyethylene terephthalate fibers (e.g., medical grade Dacron) having a high stiffness and high strength are preferred. Other polymers such as aromatic polymers (e.g., aromatic polymer of DuPont having a Kevlar tensile modulus of $10\times10^6$ psi) may also be useful in small fiber form. Thus, multistrand sutures may be provided which have a high degree of flexibility together with long-term biocompatability and physical integrity.

Having generally described the multistrand sutures of the present invention, the invention will now be more particularly described with respect to the particular embodiments illustrated in the drawings.

Illustrated in FIG. 1 is an illustration of a shape of operative procedure for correction of truncus arteriosus in which patch closure of the ventricular septal defect is begun by means of a small diameter multistrand suture 10. The suture 10 comprises a braided array of a plurality of small diameter carbon coated fibers. In the illustrated embodiment, an enlarged view of a portion of suture 10 is shown in FIG. 2. The multistrand suture 10 comprises a plurality of 50 individual fibers 12 each having a diameter of about 10 microns. The illustrated multistrand suture accordingly has a diameter of about 100 microns (0.004 inches).

The individual substrate fibers 12 are of circular cross-section and are made of axially oriented polyethylene terephthalate. The individual substrate fibers 12 have a tensile strength of about 40,000 psi and a tensile modulus of about $2 \times 10^6$ psi.

The substrate fibers 12 of the multistrand suture 10 have an adherent, carbon surface coating. The coating on the fibers is isotropic carbon having a BAF of about 1.3 or less and a maximum thickness of about 3000 Angstroms over fibers at the exterior surface of the braided array. The illustrated suture 10 is coated with carbon in finished, braided form, so that the coating thickness on the fibers tends to decrease at the surfaces of the substrate fibers toward the interior of the braided suture 10. Although the fibers of the braided array are coated together in finished form, the fibers are individually coated by the deposition process, and are not substantially bonded together.

In use, the suture 10 is flexible and fatigue resistant and is biologically compatible in the implantation environment. Further, the braided structure of the graft permits some tissue ingrowth to provide for effective and natural fixation of the permanent suture through immobilization in the sutured tissue. Further, while the carbon coating may be cracked under very high strain areas at suture knots, the carbon coating generally maintains its integrity under conditions of flexure and tensile strain.

Illustrated in FIG. 3 is an embodiment 20 of a small diameter carbon-coated multistrand suture comprising needle 22 and braided strand 24 of polyethylene terephthalate fibers, which is shown in operative procedure for perineural suture of lacerated nerve 26. Another example of the use of sutures in accordance with the present invention where permanent retention of a strong, functional suture is appropriate, is the suturing of tendons. A suitable suture for tendon attachment comprises a plurality of 100 small organpolymeric fibers each having a circular cross-section and a diameter of about 5 microns. The fibers may be twisted into a plurality of three substrands which, in turn may be twisted into a multistrand suture array. The preformed multistrand suture substrate is coated in a manner such as that of U.S. Pat. No. 3,952,334, and coating is carried out until a thickness of about 3000 Angstroms of carbon is deposited on the surfaces of the individual fibers at the exterior of the suture 20, with decreasing thickness toward the interior of the suture. The carbon coating is smooth and uniform, and has a density of about 1.8 gm/cm³, a BAF of about 1.2, and a tensile strain at fracture which is greater than 5 percent.

Like the fibers of the embodiment 10 of FIG. 1, the substrate fibers of the suture 20 or other sutures such as a tendon or heart valve suture are individually coated with the carbon coating and are not substantially bonded together. The individual fibers are thus free to bend and glide over each other in the flexure of the suture. The sutures have excellent compatability with blood and tissue at the suture site.

It will be appreciated that in accordance with the present invention, multistrand sutures have been provided which are particularly adapted for prolonged or permanent implantation in the living body, which are biologically inert, which have substantial tensile strength, and which are capable of substantial flexible motion in service.

Although the invention has been described with regard to certain preferred embodiments, it should be understood that various modifications and adaptations may be made based on the present disclosure which should be regarded to be within the spirit and scope of the present invention.

Various of the features of the invention are set forth in the following claims.

What is claimed is:

1. A suture assembly for applying a flexible, fatigue resistant and biologically compatible multistrand suture in prolonged or permanent implantation in a living body comprising
    a suture needle and connected thereto for surgical suturing procedure,
    a fiber substrate array of a plurality of at least about 7 organopolymeric fibers having a tensile modulus of elasticity of about $2 \times 10^6$ psi or more, and a fiber diameter of less than about 25 microns, and a dense, adherent, isotropic carbon coating on the fibers having a BAF of about 1.3 or less, a thickness of less than about 7000 Angstroms, and a relatively high tensile fracture strain of at least about 5 percent, said fibers being individually coated with said carbon coating such that they are free to bend and glide over each other in flexure of the suture, said tensile fracture strain, said tensile modulus of elasticity and said fiber diameter providing the suture with a predetermined high degree of flexibility and strength suitable for implantation by suturing without substantial cracking of said coating along the suture.

2. A suture assembly in accordance with claim 1 wherein said substrate array is a helically twisted array of said fibers.

3. A suture assembly in accordance with claim 2 wherein the substrate fiber is polyethylene terephthalate.

4. A suture assembly in accordance with claim 2 wherein the array is a braided array of said fibers.

5. A suture assembly in accordance with claim 1 wherein said fibers have a diameter of about 10 microns and wherein said coating thickness is in the range of from about 3000 Angstroms to about 5000 Angstroms, and wherein said predetermined degree of flexibility is provided by each of said fibers having a minimum radius of curvature R without fracture of said coating of about 0.01 cm.

* * * * *